US012751695B2

(12) United States Patent
Amadou et al.

(10) Patent No.: US 12,751,695 B2
(45) Date of Patent: Oct. 6, 2026

(54) AI-BASED ULTRASOUND NAVIGATION SYSTEM FOR NAVIGATING TO TARGET POSITIONS DEFINED BY TEXT OR IMAGES

(71) Applicant: Siemens Medical Solutions USA, Inc., Malvern, PA (US)

(72) Inventors: Abdoul Aziz Amadou, London (GB); Vivek Singh, Princeton, NJ (US); Puneet Sharma, Princeton Junction, NJ (US); Florin-Cristian Ghesu, Baiersdorf (DE); Young-Ho Kim, West Windsor, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 18/822,586

(22) Filed: Sep. 3, 2024

(65) Prior Publication Data

US 2026/0060649 A1 Mar. 5, 2026

(51) Int. Cl.

*A61B 8/00* (2006.01)
*G06N 3/08* (2023.01)
*G06T 1/00* (2006.01)
*G06N 20/00* (2019.01)
*G06T 7/33* (2017.01)

(Continued)

(52) U.S. Cl.

CPC ........... *A61B 8/4263* (2013.01); *A61B 8/461* (2013.01); *G06N 3/08* (2013.01); *G06T 1/00* (2013.01); *G06N 20/00* (2019.01); *G06T 7/33* (2017.01); *G06T 17/00* (2013.01); *G06V 10/40* (2022.01); *G06V 2201/03* (2022.01)

(58) Field of Classification Search

CPC ........ A61B 8/4263; A61B 8/461; G06N 3/08; G06N 20/00; G06T 1/00; G06T 7/33; G06T 17/00; G06V 10/40; G06V 2201/03

See application file for complete search history.

(56) References Cited

U.S. PATENT DOCUMENTS

2017/0360403 A1* 12/2017 Rothberg ............... A61B 8/085
2021/0104313 A1* 4/2021 Mizobe ................ G06N 3/0475
2022/0386990 A1* 12/2022 Rothberg ............. A61B 8/0883

OTHER PUBLICATIONS

Li et al., "RL-TEE: Autonomous Probe Guidance for Transesophageal Echocardiography Based on Attention-Augmented Deep Reinforcement Learning", IEEE Transactions on Automation Science and Engineering, 2023, pp. 1526-1538.

(Continued)

*Primary Examiner* — Joel Lamprecht
*Assistant Examiner* — James F McDonald, III

(57) ABSTRACT

Systems and methods for automatically navigating a medical image acquisition device are provided. 1) An initial image depicting a current position of a medical image acquisition device and 2) at least one of a target image depicting a target position of the medical image acquisition device or text-based instructions for navigating to the target position of the medical image acquisition device are received. Features are extracted from the at least one of the target image or the text-based instructions respectively using at least one of a machine learning based image encoder or a machine learning based text encoder. One or more actions for navigating the medical image acquisition device from the current position towards the target position are determined according to a learned policy based on the initial image and the extracted features. The one or more actions are output.

18 Claims, 10 Drawing Sheets

200

(51) Int. Cl.
*G06T 17/00* (2006.01)
*G06V 10/40* (2022.01)

(56) References Cited

OTHER PUBLICATIONS

Amadou et al., "Cardiac ultrasound simulation for autonomous ultrasound navigation", Frontiers in Cardiovascular Medicine, 2024, pp. 1-17.
Radford et al., "Learning Transferable Visual Models From Natural Language Supervision", arXivP2103.00020v1, 2021, pp. 1-48.
Myers et al., "Goal Representations for Instruction Following: A Semi-Supervised Language Interface to Control", arXiv:2307.00117v2, 2023, pp. 1-15.
Eysenbach et al., "Contrastive Learning as Goal-Conditioned Reinforcement Learning", arXiv:2206.07568v2, 2023, pp. 1-29.
Amadou et al., "Goal-conditioned reinforcement learning for ultrasound navigation guidance", arXiv:2405.01409v3, 2024, pp. 1-11.
U.S. Appl. No. 18/432,113, "Contrastive Reinforcement Learning-Based Navigation in Medical Imaging", filed Feb. 5, 2024.

* cited by examiner

400

AI-BASED ULTRASOUND NAVIGATION SYSTEM FOR NAVIGATING TO TARGET POSITIONS DEFINED BY TEXT OR IMAGES

TECHNICAL FIELD present invention relates generally to an AI/ML (artificial intelligence/machine learning)-based ultrasound navigation system, and more specifically to an AI/ML-based ultrasound navigation system for navigating to target positions defined by text or images.

BACKGROUND

Ultrasound is a medical imaging technique that uses high-frequency sound waves to produce images of structures within the body of a patient. Ultrasound is often used for diagnostic and interventional purposes due to its low cost, accessibility, and lack of ionizing radiation. Ultrasound allows clinicians to assess organ functionality and structure in real-time, which can provide useful information in diagnostic settings and complement other imaging modalities in interventional settings.

The quality of ultrasound images can be significantly influenced by the skill and experience of the operator. However, there are currently not enough skilled operators to meet the increasing demand, as operator training is a time-consuming process. Recently, machine learning based networks have been proposed for automatically navigating ultrasound systems to target positions on the patient. However, such conventional machine learning based networks are trained to navigate to only a single target position and hence each target position would require a dedicated network.

BRIEF SUMMARY OF THE INVENTION

In accordance with one or more embodiments, systems and methods for automatically navigating a medical image acquisition device are provided. 1) An initial image depicting a current position of a medical image acquisition device and 2) at least one of a target image depicting a target position of the medical image acquisition device or text-based instructions for navigating to the target position of the medical image acquisition device are received. Features are extracted from the at least one of the target image or the text-based instructions respectively using at least one of a machine learning based image encoder or a machine learning based text encoder. The machine learning based image encoder and the machine learning based text encoder are trained to generate corresponding features for training target images and training text-based instructions for same target positions. One or more actions for navigating the medical image acquisition device from the current position towards the target position are determined according to a learned policy based on the initial image and the extracted features. The one or more actions are output.

In one embodiment, the machine learning based image encoder and the machine learning based text encoder are trained to maximize a similarity between the features extracted from the training target images and the features extracted from the training text-based instructions. In another embodiment, the machine learning based image encoder and the machine learning based text encoder are trained to minimize a similarity between the features extracted from the training target images and features extracted from randomly sampled training text-based instructions.

In one embodiment, the one or more actions are determined using a machine learning based policy network. The machine learning based policy network receives as input the initial image and the extracted features and generates as output the one or more actions.

In one embodiment, features are extracted from the initial image using another machine learning based image encoder. The one or more actions are determined using a machine learning based policy network. The machine learning based policy network receives as input the features extracted from the initial image and the features extracted from the at least one of the target image or the text-based instructions and generates as output the one or more actions.

In one embodiment, the one or more actions are determined using a machine learning based policy network. The machine learning based policy network is trained based on training initial images and features extracted from the training target images using the machine learning based image encoder to learn the learned policy.

In one embodiment, the training text-based instructions are generated based on trajectory descriptions representing paths between initial images and target images. The trajectory descriptions are generated by: segmenting one or more anatomical objects from the initial images and the target images; generating summaries of the initial images and the target images based on the segmentations; and generating the trajectory descriptions based on the generated summaries of the initial images and the target images using a language model.

In one embodiment, the medical image acquisition device comprises a transducer of an ultrasound imaging system.

In one embodiment, the text-based instructions comprise natural language text.

These and other advantages of the invention will be apparent to those of ordinary skill in the art by reference to the following detailed description and the accompanying drawings.

DETAILED DESCRIPTION

The present invention generally relates to AI/ML based ultrasound navigation systems and methods for navigating to target locations defined by text or images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for an AI/ML-based navigation system. The navigation system automatically navigates an ultrasound transducer towards a target position of a patient for acquiring ultrasound images at the target position. The target position may be defined by a target image and/or natural language text-based instructions as input to the ultrasound navigation system. The navigation system is trained first with contrastive pretraining to train an image encoder and a text encoder to extract matching features from training target images and training text-based instructions defining the same target positions. The navigation system is then trained with contrastive reinforcement learning for learning a policy for determining one or more actions for navigating the ultrasound transducer towards the target position. Once trained, the navigation system is deployed in a clinical setting for automatically navigating the ultrasound transducer towards the target position defined by a target image and/or natural language text-based instructions. Advantageously, the navigation system enables natural language text-based instructions as input to better supports clinicians in both diagnostic and interventional scenarios by allowing the clinicians to specify the target location using language commands.

Figure 1:
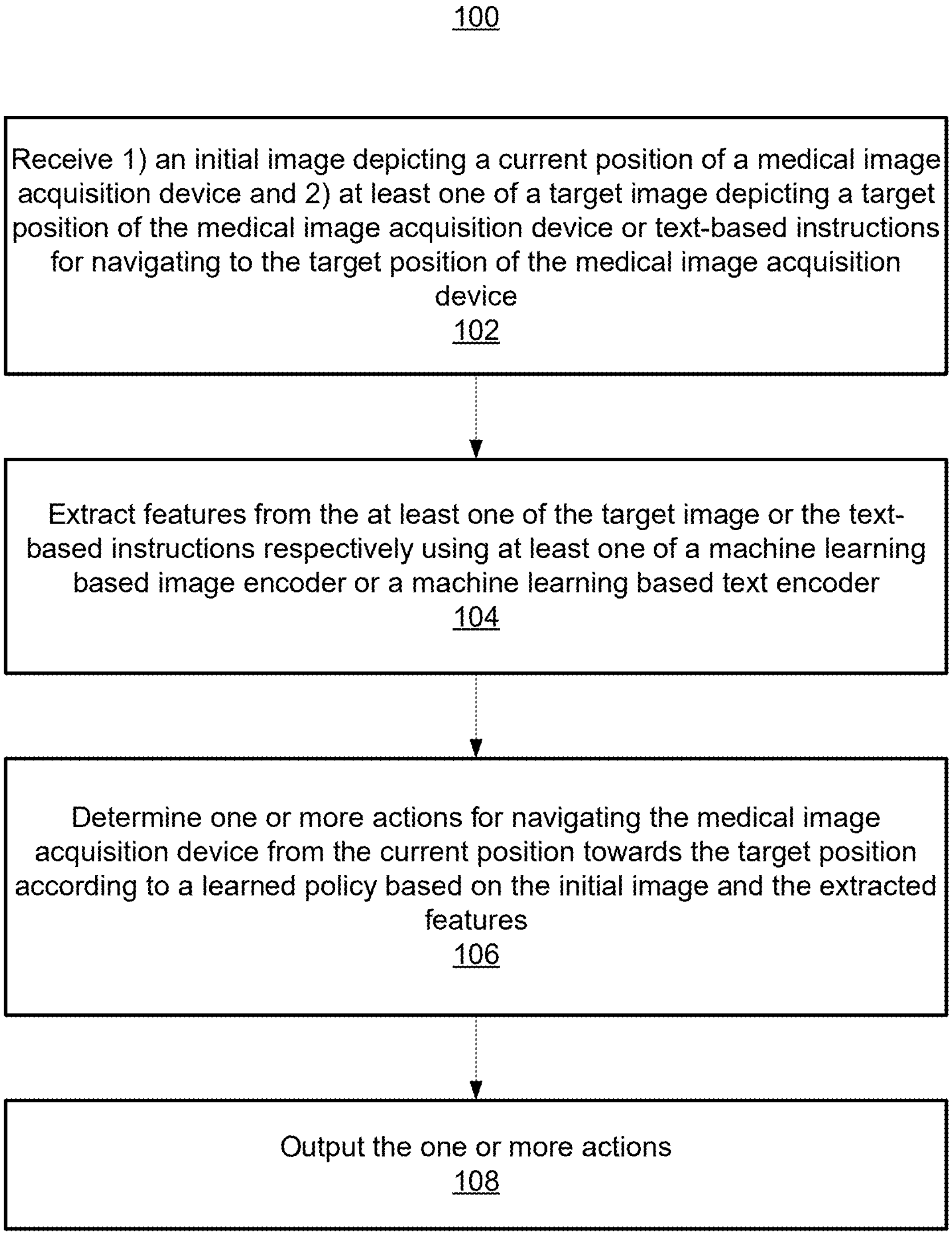
FIG. 1 shows a method for automatically navigating an image acquisition device using an AI/ML based navigation system, in accordance with one or more embodiments.
Figure 2:
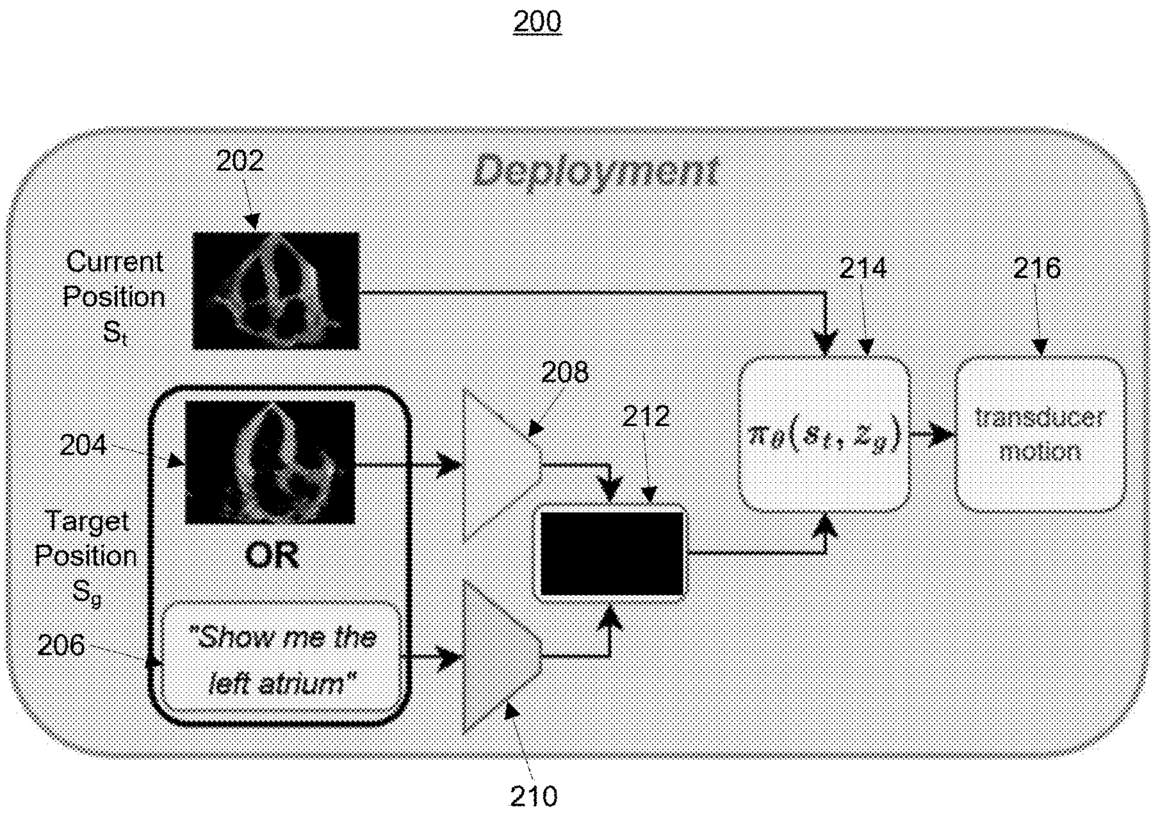
FIG. 2 shows a workflow of a deployment stage of the AI/ML based navigation system for automatically navigating an image acquisition device, in accordance with one or more embodiments.

FIG. 1 shows a method 100 for automatically navigating an image acquisition device using an AI/ML based navigation system, in accordance with one or more embodiments. The steps and sub-steps of method 100 may be performed by one or more suitable computing devices, such as, e.g., computer 1002 of FIG. 10. FIG. 2 shows a workflow 200 of a deployment stage of the AI/ML based navigation system for automatically navigating an image acquisition device, in accordance with one or more embodiments. FIG. 1 and FIG. 2 will be described together.

At step 102 of FIG. 1, 1) an initial image depicting a current position of a medical image acquisition device and 2) at least one of a target image depicting a target position of the medical image acquisition device or text-based instructions for navigating to the target position of the medical image acquisition device are received. In one example, as shown in workflow 200 of FIG. 2, the initial image is initial image 202 depicting current position $S_t$, the target image is target image 204 depicting target position $S_g$, and the text-based instructions are text-based instructions 206 describing the target position $S_g$.

The initial image depicts a view of the medical image acquisition device at the current position and represents the current state of the medical image acquisition device. The target image is a view of an anatomical object that the medical image acquisition device would depict at the target position and represents the target or goal state of the medical image acquisition device. The target image may be a preoperative image of the anatomical object, obtained from any patient or a synthetic image generated from an image of another modality. The anatomical object may comprise, for example, organs, bones, vessels, tumors or other abnormalities, or any other anatomical object of interest.

In one embodiment, the initial image and the target image are ultrasound images and the medical image acquisition device is an ultrasound imaging device. In this embodiment, the initial position and the target position represent positions of a transducer or probe of the ultrasound imaging device. However, the initial image, the target image, and the medical image acquisition device may be of any other suitable modality, such as, e.g., MRI (magnetic resonance imaging), PET (positron emission tomography), SPECT (single photon emission computed tomography), CT (computed tomography), x-ray, or any other medical imaging modality or combinations of medical imaging modalities. The current image and/or the target image may be 2D (two dimensional) images and/or 3D (three dimensional) volumes, and may comprise a single input medical image or a plurality of input medical images.

The text-based instructions comprise natural language text-based instructions for navigating to the anatomical object that the medical image acquisition device would depict at the target position. For example, as shown in workflow 200 of FIG. 2, text-based instructions 206 is the text-based instruction "show me the left atrium." In one embodiment, speech is received from a user (e.g., via a microphone) and the speech is converted to the text-based instruction using, e.g., any well-known text-to-speech approach.

Figure 10:
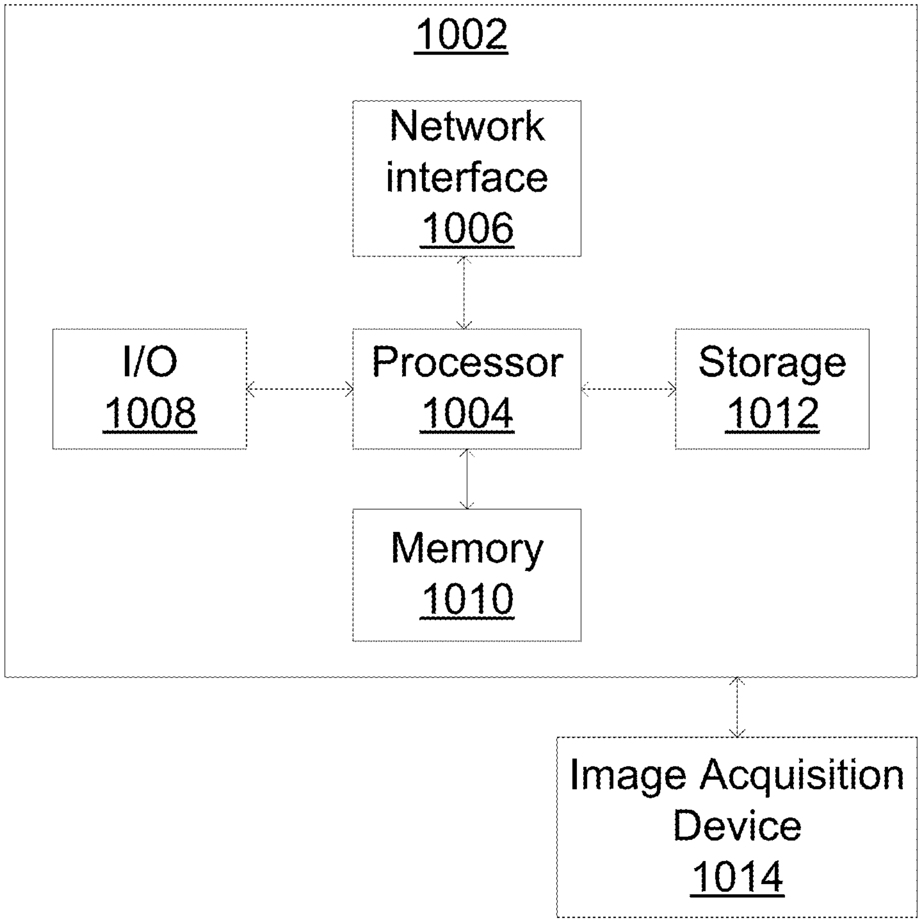
FIG. 10 shows a high-level block diagram of a computer that may be used to implement one or more embodiments.

The initial image, the target image, and/or the text-based instructions may be received, for example, by directly receiving the images from the medical image acquisition device (e.g., image acquisition device 1014 of FIG. 10) as the images are acquired, by loading the images and/or text from a storage or memory of a computer system (e.g., storage 1012 or memory 1010 of computer 1002 of FIG. 10), or by receiving the images and/or text from a remote computer system (e.g., computer 1002 of FIG. 10). Such a computer system or remote computer system may comprise one or more patient databases, such as, e.g., an EHR (electronic health record), EMR (electronic medical record), PHR (personal health record), HIS (health information system), RIS (radiology information system), PACS (picture archiving and communication system), LIMS (laboratory information management system), or any other suitable database or system. In one embodiment, the target image is selected from a library of images.

At step 104 of FIG. 1, features are extracted from the at least one of the target image or the text-based instructions respectively using at least one of a machine learning based image encoder or a machine learning based text encoder. In one example, as shown in workflow 200 of FIG. 2, features $Z_g$ 212 are extracted from at least one of target image 204 or text-based instructions 206 respectively using at least one of image encoder 208 or text encoder 210. The features are compact, fixed-size representations (e.g., vectors) of the target image and/or the text-based instructions that captures important aspects of the target image and/or text-based instructions.

The machine learning based image encoder and the machine learning based text encoder are jointly trained during a prior offline or training stage to generate corresponding features for training target images and training text-based instructions for same target positions. In one embodiment, the machine learning based image encoder and the machine learning based text encoder are trained as described with respect to FIGS. 3 and 4, explained in detail below. Once trained, the machine learning based image encoder and/or the machine learning based text encoder are applied during an online or inference stage, e.g., to perform step 104 of FIG. 1.

The machine learning based image encoder receives as input the target image and generates as output the extracted features. The machine learning based image encoder may be implemented according to any suitable machine learning based architecture, such as, e.g., an autoencoder, a vision transformer, a CNN (convolutional neural network), etc.

The machine learning based text encoder receives as input the text-based instructions and generates as output the extracted features. The machine learning based text encoder may be implemented according to any suitable machine learning based architecture. In one embodiment, the machine learning based text encoder is a language model, such as, e.g., an LLM (large language model). However, the language model may be any other suitable language model. For example, the language model may be a small language model, which uses a relatively smaller neural network, has fewer parameters, and is trained on less training data as compared with an LLM.

The LLM may be any suitable pretrained deep learning based LLM. For example, the LLM may be based on the transformer architecture, which uses an attention mechanism to capture long-range dependencies in text. One example of a transformer-based architecture is GPT (generative pre-training transformer), which has a multilayer transformer decoder architecture that may be pretrained to optimize the next token prediction task and then fine-tuned with labelled data for various downstream tasks. Other exemplary transformer-based architectures include BLOOM (BigScience Large Open-science Open-access Multilingual Language Model) and BERT (Bidirectional Encoder Representations from Transformers).

At step 106 of FIG. 1, one or more actions are determined for navigating the medical image acquisition device from the current position towards the target position according to a learned policy based on the initial image and the extracted features. The one or more actions are determined by the machine learning based policy network according to the learned policy. In one example, as shown in workflow 200 of FIG. 2, one or more actions are determined using a machine learning based policy network 214 according to policy $\pi_\theta(S_t, Z_g)$ based on initial image 202 and extracted features $Z_g$.

The machine learning based policy network may be implemented using a neural network or any other suitable machine learning based architecture. The machine learning based policy network receives as input the initial image and the extracted features and generates as output the one or more actions according to the learned policy $\pi_\theta(S_t, Z_g)$. The machine learning based policy network is trained during a prior offline or training stage, e.g., using CRL (contrastive reinforcement learning) to learn the policy $\pi_\theta(S_t, Z_g)$. In one embodiment, the machine learning based policy network is trained according to FIGS. 3 and 5, explained in detail below.

The one or more actions comprise a change in the current state of the medical image acquisition device and/or its field of view, such as, e.g., a change in position, location, and/or orientation. The one or more actions may be one of a sequence of steps to reach the target position. In one example, the one or more actions $\alpha_t$ may comprise a translation along the x, y, and/or z axes, a rotation around the x, y, and/or z axes, or a combination thereof for navigating the medical image acquisition device from the current position towards the target position in one, two, or three dimensions.

In one embodiment, instead of the machine learning based policy network directly receiving as input the initial image, features are first extracted from the initial image using another machine learning based image encoder. The machine learning based policy network then receives as input the features extracted from the initial image and the features $Z_b$ extracted from the at least one of the target image or the text-based instructions and generates as output the one or more actions at.

At step 108 of FIG. 1, the one or more actions are output. For example, the one or more actions can be output by displaying the one or more actions on a display device of a computer system (e.g., I/O 1008 of computer 1002 of FIG. 10), storing the one or more actions on a memory or storage of a computer system (e.g., memory 1010 or storage 1012 of computer 1002 of FIG. 10), or by transmitting the one or more actions to a remote computer system (e.g., computer 1002 of FIG. 10).

In one embodiment, the one or more actions are output to a medical image navigation system for automatically navigating the medical image acquisition device from the current position towards the target position according to the one or more actions. In one example, as shown in workflow 200 of FIG. 2, the one or more actions determined by machine learning based policy network 214 are output to an ultrasound navigation system to navigate the probe according to the one or more actions, resulting in transducer motion 216.

In one embodiment, for example where the medical image acquisition device is not located at the target position after navigating according to the one or more actions, method 100 of FIG. 1 may be repeated for one or more iterations using an image acquired at the location the medical image acquisition device was navigated to (according to the one or more actions) as the initial image. In this manner, the medical image acquisition device is iteratively navigated until it reaches the target position.

Figure 3:
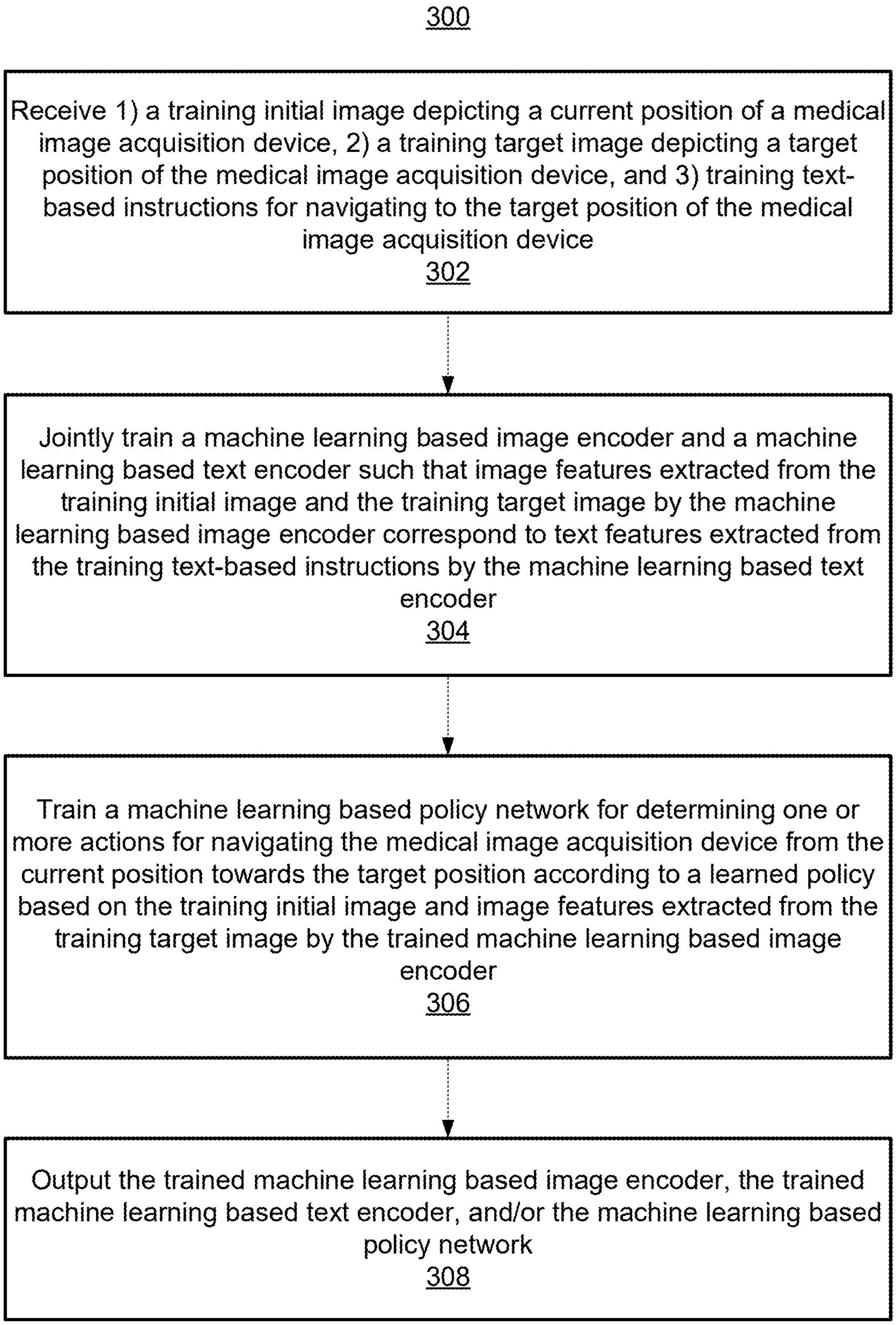
FIG. 3 shows a method for training an AI/ML based navigation system for automatically navigating an image acquisition device, in accordance with one or more embodiments.
Figure 4:
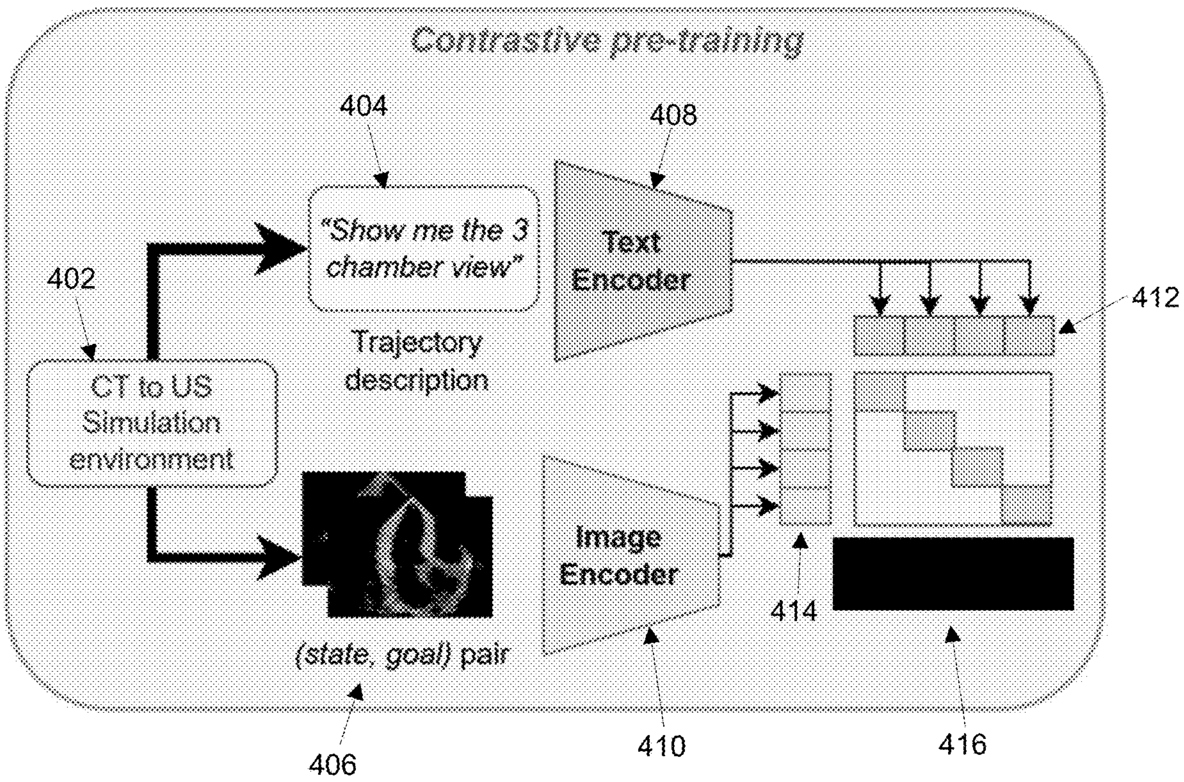
FIG. 4 shows a workflow of a contrastive pre-training stage for jointly training a machine learning based image encoder and a machine learning based text encoder of the AI/ML based navigation system, in accordance with one or more embodiments.
Figure 5:
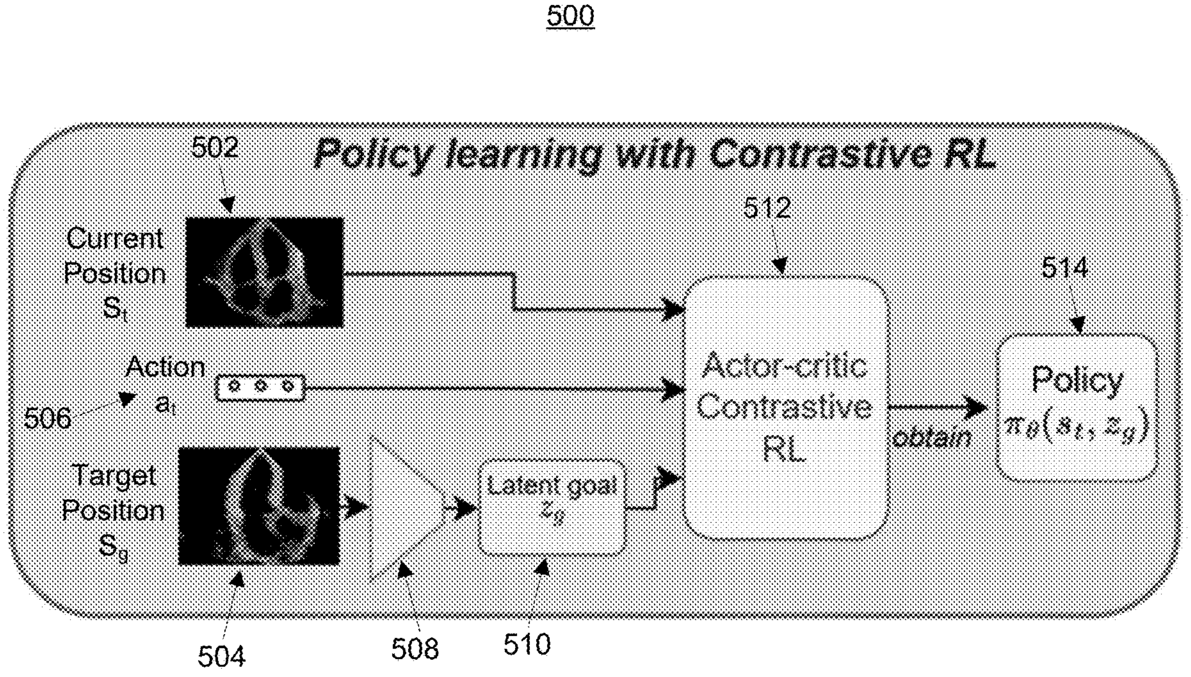
FIG. 5 shows a workflow of a policy learning with contrastive RL (reinforcement learning) stage for training a machine learning based policy network of the AI/ML based navigation system, in accordance with one or more embodiments.

FIG. 3 shows a method 300 for training an AI/ML based navigation system for automatically navigating an image acquisition device, in accordance with one or more embodiments. The steps and sub-steps of method 300 may be performed by one or more suitable computing devices, such as, e.g., computer 1002 of FIG. 10. FIG. 4 shows a workflow 400 of a contrastive pre-training stage for jointly training a machine learning based image encoder and a machine learning based text encoder of the AI/ML based navigation system, in accordance with one or more embodiments. FIG. 5 shows a workflow 500 of a policy learning with contrastive RL (reinforcement learning) stage for training a machine learning based policy network of the AI/ML based navigation system, in accordance with one or more embodiments. FIG. 3-5 will be described together.

At step 302 of FIG. 3, 1) a training initial image depicting a current position of a medical image acquisition device, 2) a training target image depicting a target position of the medical image acquisition device, and 3) training text-based instructions for navigating to the target position of the medical image acquisition device are received. In one example, as shown in workflow 400 of FIG. 4, the training initial image and the training target image are shown as (state, goal) pair 406 and the training text-based instructions are training text-based instructions 404. In one embodiment, workflow 400 is performed in a CT to US (ultrasound) simulation environment 402, where the training initial image and the training target image of (state, goal) pair 406 are synthetic ultrasound images generated from CT images for a given transducer position. In another example, as shown in workflow 500 of FIG. 5, the training initial image is training initial image 502 corresponding to current position $S_t$ and the training target image is training target image 504 corresponding to target position $S_g$.

The training initial image depicts a view of the medical image acquisition device at the current position. The training target image depicts a view of an anatomical object that the medical image acquisition device would depict at the target position. The training text-based instructions comprises natural language text-based instructions describing the anatomical object that the medical image acquisition device would depict at the target position. The training target image depicts, and the training text-based instructions describe, the same target position and thus the training target image corresponds with the training text-based instructions.

In one embodiment, the training initial image and the training target image are ultrasound images and the medical image acquisition device is an ultrasound imaging device. However, the training initial image, the training target image, and the medical image acquisition device may be of any other suitable modality. The training initial image and/or the training target image may be 2D images and/or 3D volumes, and may comprise a single input medical image or a plurality of input medical images. In one embodiment, the training current image and/or the training target image may be synthetic images generated from images of a different modality (e.g., using a GAN (generative adversarial network)) for a given transducer position.

The training initial image, the training target image, and/or the training text-based instructions may be received, for example, by directly receiving the images from the medical image acquisition device (e.g., image acquisition device 1014 of FIG. 10) as the images are acquired, by loading the images and/or text from a storage or memory of a computer system (e.g., storage 1012 or memory 1010 of computer 1002 of FIG. 10), or by receiving the images and/or text from a remote computer system (e.g., computer 1002 of FIG. 10).

At step 304 of FIG. 3, a machine learning based image encoder and a machine learning based text encoder are jointly trained such that image features extracted from the training initial image and the training target image by the machine learning based image encoder correspond to text features extracted from the training text-based instructions by the machine learning based text encoder. In one example, the machine learning based image encoder and the machine learning based text encoder are the machine learning based image encoder and the machine learning based text encoder utilized at step 104 of FIG. 1 or are the image encoder 208 and text encoder 210 of FIG. 2, respectively. In another example, as shown in workflow 400 of FIG. 4, the machine learning based image encoder is image encoder 410 and the machine learning based text encoder is text encoder 408. Image encoder 410 and text encoder 408 are jointly trained such that image features 414 extracted from (state, goal) pair 406 by image encoder 410 correspond to text features 412 extracted from training text-based instructions 404 by text encoder 408, thereby resulting in feature alignment 416.

The machine learning based text encoder is trained based on training text-based instructions. The training text-based instructions may be generated from descriptions of trajectories representing paths between training initial images and training target images. The trajectory descriptions are text explaining changes in anatomy between the training current images and the training target images, and may optionally include descriptions of one or more actions of the medical image acquisition device applied to navigate from the current position to the target position.

In one embodiment, the machine learning based image encoder and the machine learning based text encoder are trained according to CLIP. The machine learning based image encoder receives the training initial image and the training target image as input and generates image features as output. The machine learning based text encoder receives the training text-based instructions as input and generates text features as output. The machine learning based image encoder and the machine learning based text encoder are trained to generate corresponding image features and text features respectively. The image features and the text features correspond when they are the same or similar to each other.

The machine learning based image encoder and the machine learning based text encoder are trained using contrastive learning using pairs of similar and dissimilar images/text-based instructions. Given corresponding (state, goal, text-based instructions) triplets, the machine learning based image encoder and the machine learning based text encoder are trained to maximize the similarity (e.g., measured by a dot product) between the image features and text features, while minimizing the similarity between the image features and text features extracted from randomly sampled text-based instructions.

At step 306 of FIG. 3, a machine learning based policy network is trained for determining one or more actions for navigating the medical image acquisition device from the current position towards the target position according to a learned policy based on the training initial image and image features extracted from the training target image by the trained machine learning based image encoder. The trained machine learning based image encoder is frozen at this step. In one example, the machine learning based policy network is the machine learning based policy network utilized at step 106 of FIG. 1. In another example, as shown in workflow 500 of FIG. 5, machine learning based policy network is trained based on actor-critic contrastive RL 512 based on training initial image 502 corresponding to current position $S_t$, image features 510 extracted from training target image 504 using image encoder 508, and a set of actions $\alpha_t$ 506 to learn policy $\pi_\theta(S_t, Z_g)$ 514. Image encoder 508 is the trained image encoder 410 of FIG. 4.

The machine learning based policy network is trained using GCRL (goal-conditioned reinforcement learning) in an actor-critic framework. In the actor-critic framework, a machine learning based critic network is trained with a critic loss and a machine learning based actor network is trained with an actor loss, so that the critic network and actor network are sequentially or iteratively trained (i.e., fixing one network while training the other). The actor network includes the machine learning based policy network. To train the actor network, the output of the policy network is input to the critic network to generate a probability as the actor loss. The actor loss is used as a reward in optimization of the learnable parameters of the policy network to generate one or more actions leading to the target position. The policy network is trained on the loss generated from the critic network. The critic network is trained according to CRL based on training initial images, target images, and actions sampled from a set of trajectories representing possible paths between the current position and the target position. Further details on training of the machine learning based policy network are described in U.S. patent application Ser. No. 18/432,113, filed Feb. 5, 2024, the disclosure of which is incorporate herein by reference in its entirety.

At step 308 of FIG. 3, the trained machine learning based image encoder, the trained machine learning based text encoder, and/or the machine learning based policy network are output. For example, the trained machine learning based image encoder, the trained machine learning based text encoder, and/or the machine learning based policy network can be output by storing the trained machine learning based image encoder, the trained machine learning based text encoder, and/or the machine learning based policy network on a memory or storage of a computer system (e.g., memory 1010 or storage 1012 of computer 1002 of FIG. 10) or by transmitting the trained machine learning based image encoder, the trained machine learning based text encoder, and/or the machine learning based policy network to a remote computer system (e.g., computer 1002 of FIG. 10).

In one embodiment, the trajectory descriptions utilized (e.g., at 304 of FIG. 3) for training the machine learning based text encoder (e.g., the machine learning based text encoder of step 104 of FIG. 1, text encoder 210 of FIG. 2, and/or text encoder 408 of FIG. 4) may be automatically generated. The trajectory descriptions are used to generate the training text-based instructions.

Given segmentations of anatomical objects from images other modalities (e.g., CT images) and a given current position of the medical image acquisition device, a synthetic (e.g., ultrasound) image is generated (e.g., using a GAN). Since segmentations are readily available, they can be reused to generate trajectory descriptions. While the generation of the trajectory descriptions are described herein using synthetic ultrasound images, the text-based instructions and trajectory descriptions may also be generated by collecting and annotating medical images. To generate the trajectory descriptions, standalone images are first described or summarized. The trajectory descriptions are then generated by combining the separate descriptions from a training initial image, training target image, and actions.

Images are described or summarized by describing the anatomical features depicted in the images. For example, the description may be "This is a four-chamber view. The left atrium is at the far field of the image, on the right side, etc." The description may be obtained directly from the segmentations as the organs that are in the field of view are known, as well as their spatial location. The image descriptions are named as a template denoted by T. This template is an exhaustive description of all the organs and structures depicted in a given image. Thus $T_0$ would be the template corresponding to image $S_0$.

The trajectory descriptions are then generated by combining the image descriptions. In one embodiment, a language model (e.g., LLM) is utilized. Using in-context learning (i.e., by describing the task to the language model), the language model may be prompted to generate the text-based instructions. The language model is input with template descriptions $T_0$, $T_g$ for the initial image and the target image, along with a description of one or more actions $T_A$ applied to navigate from the current position to the target position. Formally, the text-based instructions $T_D$ are obtained as $T_D$=LLM ($T_0$, $T_g$, $T_A$). To prompt the language model, given the triplet ($T_0$, $T_g$, $T_A$), trajectory descriptions of the following types may be generated: 1) standalone descriptions, 2) action description, 3) action description and anatomical content, and 4) anatomical content.

Standalone descriptions: The language model is prompted to summarize either template descriptions $T_0$ or $T_g$. The input to the image encoder will be either the current image or the target image, and the channel corresponding to the other image is masked. This enables the reuse of the image encoder to allow the image encoder to encode a single target image when learning the policy. The language model may be prompted to generate multiple textual descriptions to cover a wide range of potential descriptions given the template. For example, the input template may provide: "This is a four chamber view. The left atrium, right atrium, left ventricle, and right ventricle are present. The left ventricle is located at the near-field on the right side of the image." For the given input template, the language model may output various descriptions, such as, e.g., "This is a four chamber view" or "The heart chambers visible int his image are the left and right atriums, and the left and right ventricles" or "The left ventricle is visible on the right side of the image."

Action description: The language model may be prompted to paraphrase template description $T_A$, such that the one or more actions that occur between the initial image and the target image are encoded. An example of the output of the language model may be: "Rotate the transducer in-plane by 15 degrees."

Action description and anatomical content: The language model may be prompted to combine template descriptions $T_A$ and $T_g$ to generate a description combining the transducer motion with some text indicating changes in anatomy. An example would be: "Rotate the transducer in-plane by 15 degrees to show the left atrium." This implies the anatomy described should not be in $T_0$ and should appear only in $T_g$.

Anatomical content: The language model may be prompted to combine template descriptions $T_0$ and $T_g$ to describe changes in anatomy. An example may be: "Show me the left atrium." This implies the anatomy described should not be in $T_0$ and should appear only in $T_g$.

Embodiments described herein may be adapted to any language using existing translation methods and is not limited to English.

Embodiments described herein are described with respect to the claimed systems as well as with respect to the claimed methods. Features, advantages or alternative embodiments herein can be assigned to the other claimed objects and vice versa. In other words, claims and embodiments for the systems can be improved with features described or claimed in the context of the respective methods. In this case, the functional features of the method are implemented by physical units of the system.

Furthermore, certain embodiments described herein are described with respect to methods and systems utilizing trained machine learning models, as well as with respect to methods and systems for providing trained machine learning models. Features, advantages or alternative embodiments herein can be assigned to the other claimed objects and vice versa. In other words, claims and embodiments for providing trained machine learning models can be improved with features described or claimed in the context of utilizing trained machine learning models, and vice versa. In particular, datasets used in the methods and systems for utilizing trained machine learning models can have the same properties and features as the corresponding datasets used in the methods and systems for providing trained machine learning models, and the trained machine learning models provided by the respective methods and systems can be used in the methods and systems for utilizing the trained machine learning models.

In general, a trained machine learning model mimics cognitive functions that humans associate with other human minds. In particular, by training based on training data the machine learning model is able to adapt to new circumstances and to detect and extrapolate patterns. Another term for "trained machine learning model" is "trained function."

In general, parameters of a machine learning model can be adapted by means of training. In particular, supervised training, semi-supervised training, unsupervised training, reinforcement learning and/or active learning can be used. Furthermore, representation learning (an alternative term is "feature learning") can be used. In particular, the parameters of the machine learning models can be adapted iteratively by several steps of training. In particular, within the training a certain cost function can be minimized. In particular, within the training of a neural network the backpropagation algorithm can be used.

In particular, a machine learning model, such as, e.g., the machine learning based image encoder and the machine learning based text encoder utilized at step 104 and the machine learning based policy network utilized at step 106 of FIG. 1, image encoder 208, text encoder 210, and policy network 214 of FIG. 2, the machine learning based image encoder and the machine learning based text encoder utilized at step 304 and the machine learning based policy network utilized at step 306 of FIG. 1 of FIG. 3, text encoder 408 and image encoder 410 of FIG. 4, and image encoder 508 of FIG. 5, can comprise, for example, a neural network, a support vector machine, a decision tree and/or a Bayesian network, and/or the machine learning model can be based on, for example, k-means clustering, Q-learning, genetic algorithms and/or association rules. In particular, a neural network can be, e.g., a deep neural network, a convolutional neural network or a convolutional deep neural network. Furthermore, a neural network can be, e.g., an adversarial network, a deep adversarial network and/or a generative adversarial network.

Figure 6:
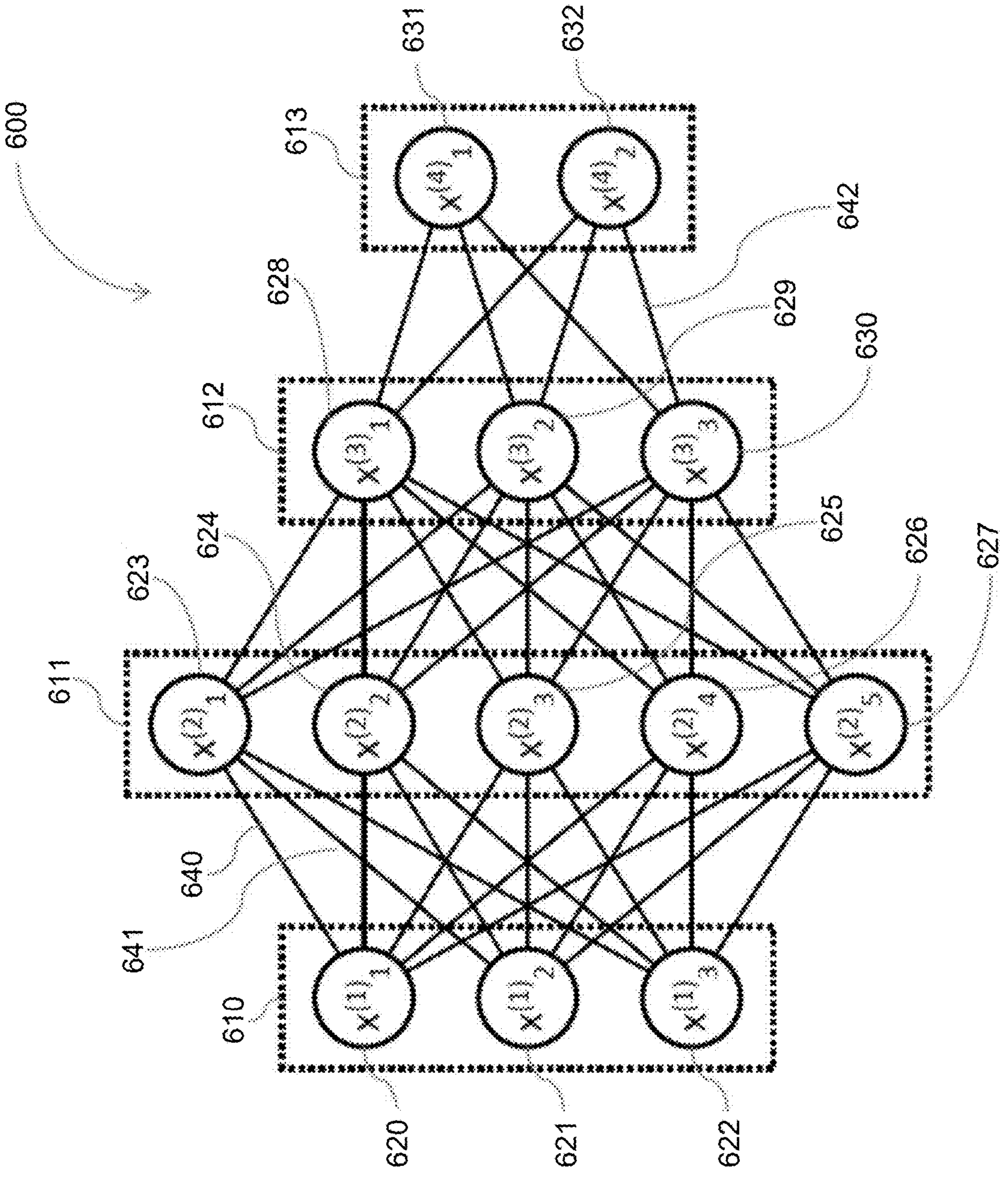
FIG. 6 shows an exemplary artificial neural network that may be used to implement one or more embodiments.

FIG. 6 shows an embodiment of an artificial neural network 600 that may be used to implement one or more machine learning models described herein. Alternative terms for "artificial neural network" are "neural network", "artificial neural net" or "neural net".

The artificial neural network 600 comprises nodes 620, . . . , 632 and edges 640, . . . , 642, wherein each edge 640, . . . , 642 is a directed connection from a first node 620, . . . , 632 to a second node 620, . . . , 632. In general, the first node 620, . . . , 632 and the second node 620, . . . , 632 are different nodes 620, . . . , 632, it is also possible that the first node 620, . . . , 632 and the second node 620, . . . , 632 are identical. For example, in FIG. 6 the edge 640 is a directed connection from the node 620 to the node 623, and the edge 642 is a directed connection from the node 630 to the node 632. An edge 640, . . . , 642 from a first node 620, . . . , 632 to a second node 620, . . . , 632 is also denoted as "ingoing edge" for the second node 620, . . . , 632 and as "outgoing edge" for the first node 620, . . . , 632.

In this embodiment, the nodes 620, . . . , 632 of the artificial neural network 600 can be arranged in layers 610, . . . , 613, wherein the layers can comprise an intrinsic order introduced by the edges 640, . . . , 642 between the nodes 620, . . . , 632. In particular, edges 640, . . . , 642 can exist only between neighboring layers of nodes. In the displayed embodiment, there is an input layer 610 comprising only nodes 620, . . . , 622 without an incoming edge, an output layer 613 comprising only nodes 631, 632 without outgoing edges, and hidden layers 611, 612 in-between the input layer 610 and the output layer 613. In general, the number of hidden layers 611, 612 can be chosen arbitrarily. The number of nodes 620, . . . , 622 within the input layer 610 usually relates to the number of input values of the neural network, and the number of nodes 631, 632 within the output layer 613 usually relates to the number of output values of the neural network.

In particular, a (real) number can be assigned as a value to every node 620, . . . , 632 of the neural network 600. Here, $x^{(n)}j$ denotes the value of the i-th node 620, . . . , 632 of the n-th layer 610, . . . , 613. The values of the nodes 620, . . . , 622 of the input layer 610 are equivalent to the input values of the neural network 600, the values of the nodes 631, 632 of the output layer 613 are equivalent to the output value of the neural network 600. Furthermore, each edge 640, . . . , 642 can comprise a weight being a real number, in particular, the weight is a real number within the interval [−1, 1] or within the interval [0, 1]. Here, $w^{(m,n)}_{i,j}$ denotes the weight of the edge between the i-th node 620, . . . , 632 of the m-th layer 610, . . . , 613 and the j-th node 620, . . . , 632 of the n-th layer 610, . . . , 613. Furthermore, the abbreviation $w^{(n)}_{i,j}$ is defined for the weight $w^{(n,n+1)}_{i,j}$.

In particular, to calculate the output values of the neural network 600, the input values are propagated through the neural network. In particular, the values of the nodes 620, . . . , 632 of the (n+1)-th layer 610, . . . , 613 can be calculated based on the values of the nodes 620, . . . , 632 of the n-th layer 610, . . . , 613 by $$x^{(n+1)}_j = f\left(\sum_i x^{(n)}_i \cdot w^{(n)}_{i,j}\right).$$

Herein, the function f is a transfer function (another term is "activation function"). Known transfer functions are step functions, sigmoid function (e.g., the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 610 are given by the input of the neural network 600, wherein values of the first hid-den layer 611 can be calculated based on the values of the input layer 610 of the neural network, wherein values of the second hidden layer 612 can be calculated based in the values of the first hidden layer 611, etc.

In order to set the values $w^{(m,n)}_{i,j}$ for the edges, the neural network 600 has to be trained using training data. In particular, training data comprises training input data and training output data (denoted as $t_i$). For a training step, the neural network 600 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 600 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left(\sum_k \delta^{(n+1)}_k \cdot w^{(n+1)}_{j,k}\right) \cdot f'\left(\sum_i x^{(n)}_i \cdot w^{(n)}_{i,j}\right)$$

based on $\delta^{(n+1)}_j$, if the (n+1)-th layer is not the output layer, and $$\delta^{(n)}_j = \left(x^{(n+1)}_j - t^{(n+1)}_j\right) \cdot f'\left(x^{(n)}_i \cdot w^{(n)}_{i,j}\right)$$

if the (n+1)-th layer is the output layer 613, wherein f' is the first derivative of the activation function, and $t^{(n+1)}_j$ is the comparison training value for the j-th node of the output layer 613.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data/image, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

By using convolutional neural networks input images can be processed in a very efficient way, because a convolution operation based on different kernels can extract various image features, so that by adapting the weights of the convolution kernel the relevant image features can be found during training. Furthermore, based on the weight-sharing in the convolutional kernels less parameters need to be trained, which prevents overfitting in the training phase and allows to have faster training or more layers in the network, improving the performance of the network.

Figure 7:
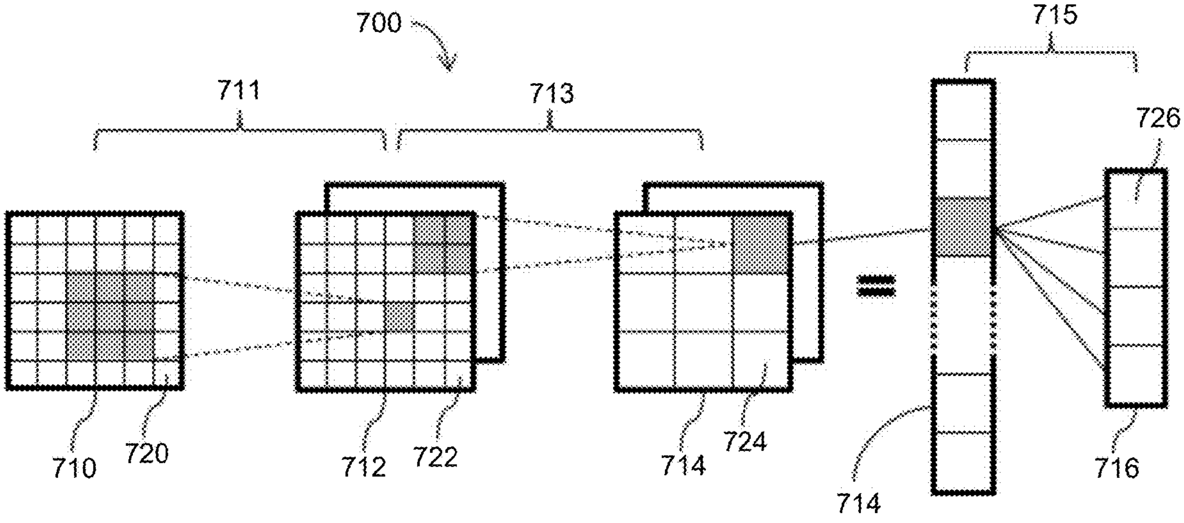
FIG. 7 shows a convolutional neural network that may be used to implement one or more embodiments.

FIG. 7 shows an embodiment of a convolutional neural network 700 that may be used to implement one or more machine learning models described herein. In the displayed embodiment, the convolutional neural network comprises 700 an input node layer 710, a convolutional layer 711, a pooling layer 713, a fully connected layer 714 and an output node layer 716, as well as hidden node layers 712, 714. Alternatively, the convolutional neural network 700 can comprise several convolutional layers 711, several pooling layers 713 and several fully connected layers 715, as well as other types of layers. The order of the layers can be chosen arbitrarily, usually fully connected layers 715 are used as the last layers before the output layer 716.

In particular, within a convolutional neural network 700 nodes 720, 722, 724 of a node layer 710, 712, 714 can be considered to be arranged as a d-dimensional matrix or as a d-dimensional image. In particular, in the two-dimensional case the value of the node 720, 722, 724 indexed with i and j in the n-th node layer 710, 712, 714 can be denoted as x(n)[i, j]. However, the arrangement of the nodes 720, 722, 724 of one node layer 710, 712, 714 does not have an effect on the calculations executed within the convolutional neural network 700 as such, since these are given solely by the structure and the weights of the edges.

A convolutional layer 711 is a connection layer between an anterior node layer 710 (with node values x(n−1)) and a posterior node layer 712 (with node values x(n)). In particular, a convolutional layer 711 is characterized by the structure and the weights of the incoming edges forming a convolution operation based on a certain number of kernels. In particular, the structure and the weights of the edges of the convolutional layer 711 are chosen such that the values x(n) of the nodes 722 of the posterior node layer 712 are calculated as a convolution x(n)=K*x(n−1) based on the values x(n−1) of the nodes 720 anterior node layer 710, where the convolution * is defined in the two-dimensional case as $$x_k^{(n)}[i, j] = (K * x^{(n-1)})[i, j] = \sum_{i'} \sum_{j'} K[i', j'] \cdot x^{(n-1)}[i - i', j - j'].$$

Here the kernel K is a d-dimensional matrix (in this embodiment, a two-dimensional matrix), which is usually small compared to the number of nodes 720, 722 (e.g., a 3×3 matrix, or a 5×5 matrix). In particular, this implies that the weights of the edges in the convolution layer 711 are not independent, but chosen such that they produce said convolution equation. In particular, for a kernel being a 3×3 matrix, there are only 9 independent weights (each entry of the kernel matrix corresponding to one independent weight), irrespectively of the number of nodes 720, 722 in the anterior node layer 710 and the posterior node layer 712.

In general, convolutional neural networks 700 use node layers 710, 712, 714 with a plurality of channels, in particular, due to the use of a plurality of kernels in convolutional layers 711. In those cases, the node layers can be considered as (d+1)—dimensional matrices (the first dimension indexing the channels). The action of a convolutional layer 711 is then a two-dimensional example defined as $$x^{(n)}_b[i, j] = \sum_a K_{a,b} * x^{(n-1)}_a[i, j] = \sum_a \sum_{i'} \sum_{j'} K_{a,b}[i', j'] \cdot x^{(n-1)}_a[i - i', j - j']$$

where x(n−1) a corresponds to the a-th channel of the anterior node layer 710, $x^{(n)}_b$ corresponds to the b-th channel of the posterior node layer 712 and $K_{a,b}$ corresponds to one of the kernels. If a convolutional layer 711 acts on an anterior node layer 710 with A channels and outputs a posterior node layer 712 with B channels, there are A·B independent d-dimensional kernels $K_{a,b}$.

In general, in convolutional neural networks 700 activation functions are used. In this embodiment re ReLU (acronym for "Rectified Linear Units") is used, with R (z)=max (0, z), so that the action of the convolutional layer 711 in the two-dimensional example is $$x^{(n)}_b[i, j] = R\left(\sum_a \left(K_{a,b} * x^{(n-1)}_a\right)[i, j]\right) = R\left(\sum_a \sum_{i'} \sum_{j'} K_{a,b}[i', j'] \cdot x^{(n-1)}_a[i - i', j - j']\right)$$

It is also possible to use other activation functions, e.g., ELU (acronym for "Exponential Linear Unit"), LeakyReLU, Sigmoid, Tanh or Softmax.

In the displayed embodiment, the input layer 710 comprises 36 nodes 720, arranged as a two-dimensional 6×6 matrix. The first hidden node layer 712 comprises 72 nodes 722, arranged as two two-dimensional 6×6 matrices, each of the two matrices being the result of a convolution of the values of the input layer with a 3×3 kernel within the convolutional layer 711. Equivalently, the nodes 722 of the first hidden node layer 712 can be interpreted as arranged as a three-dimensional 2×6×6 matrix, wherein the first dimension correspond to the channel dimension.

The advantage of using convolutional layers 711 is that spatially local correlation of the input data can exploited by enforcing a local connectivity pattern between nodes of adjacent layers, in particular by each node being connected to only a small region of the nodes of the preceding layer.

A pooling layer 713 is a connection layer between an anterior node layer 712 (with node values x(n−1)) and a posterior node layer 714 (with node values x(n)). In particular, a pooling layer 713 can be characterized by the structure and the weights of the edges and the activation function forming a pooling operation based on a non-linear pooling function f. For example, in the two-dimensional case the values x(n) of the nodes 724 of the posterior node layer 714 can be calculated based on the values x(n−1) of the nodes 722 of the anterior node layer 712 as $$x^{(n)}{}_b[i, j] = f\left(x^{(n-1)}[id_1, jd_2], \ldots , x^{(n-1)}{}_b[(i+1)d_1 - 1, (j+1)d_2 - 1]\right)$$

In other words, by using a pooling layer 713 the number of nodes 722, 724 can be reduced, by re-placing a number d1·d2 of neighboring nodes 722 in the anterior node layer 712 with a single node 722 in the posterior node layer 714 being calculated as a function of the values of said number of neighboring nodes. In particular, the pooling function f can be the max-function, the average or the L2-Norm. In particular, for a pooling layer 713 the weights of the incoming edges are fixed and are not modified by training.

The advantage of using a pooling layer 713 is that the number of nodes 722, 724 and the number of parameters is reduced. This leads to the amount of computation in the network being reduced and to a control of overfitting.

In the displayed embodiment, the pooling layer 713 is a max-pooling layer, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

In general, the last layers of a convolutional neural network 700 are fully connected layers 715. A fully connected layer 715 is a connection layer between an anterior node layer 714 and a posterior node layer 716. A fully connected layer 713 can be characterized by the fact that a majority, in particular, all edges between nodes 714 of the anterior node layer 714 and the nodes 716 of the posterior node layer are present, and wherein the weight of each of these edges can be adjusted individually.

In this embodiment, the nodes 724 of the anterior node layer 714 of the fully connected layer 715 are displayed both as two-dimensional matrices, and additionally as non-related nodes (indicated as a line of nodes, wherein the number of nodes was reduced for a better presentability). This operation is also denoted as "flattening". In this embodiment, the number of nodes 726 in the posterior node layer 716 of the fully connected layer 715 smaller than the number of nodes 724 in the anterior node layer 714. Alternatively, the number of nodes 726 can be equal or larger.

Furthermore, in this embodiment the Softmax activation function is used within the fully connected layer 715. By applying the Softmax function, the sum the values of all nodes 726 of the output layer 716 is 1, and all values of all nodes 726 of the output layer 716 are real numbers between 0 and 1. In particular, if using the convolutional neural network 700 for categorizing input data, the values of the output layer 716 can be interpreted as the probability of the input data falling into one of the different categories.

In particular, convolutional neural networks 700 can be trained based on the backpropagation algorithm. For preventing overfitting, methods of regularization can be used, e.g., dropout of nodes 720, . . . , 724, stochastic pooling, use of artificial data, weight decay based on the L1 or the L2 norm, or max norm constraints.

According to an aspect, the machine learning model may comprise one or more residual networks (ResNet). In particular, a ResNet is an artificial neural network comprising at least one jump or skip connection used to jump over at least one layer of the artificial neural network. In particular, a ResNet may be a convolutional neural network comprising one or more skip connections respectively skipping one or more convolutional layers. According to some examples, the ResNets may be represented as m-layer ResNets, where m is the number of layers in the corresponding architecture and, according to some examples, may take values of 34, 50, 101, or 152. According to some examples, such an m-layer ResNet may respectively comprise (m−2)/2 skip connections.

A skip connection may be seen as a bypass which directly feeds the output of one preceding layer over one or more bypassed layers to a layer succeeding the one or more bypassed layers. Instead of having to directly fit a desired mapping, the bypassed layers would then have to fit a residual mapping "balancing" the directly fed output.

Fitting the residual mapping is computationally easier to optimize than the directed mapping. What is more, this alleviates the problem of vanishing/exploding gradients during optimization upon training the machine learning models: if a bypassed layer runs into such problems, its contribution may be skipped by regularization of the directly fed output. Using ResNets thus brings about the advantage that much deeper networks may be trained.

A generative adversarial network or model (an acronym is GAN) comprises a generative function and a discriminative function, wherein the generative function creates synthetic data, and the discriminative function distinguishes between synthetic and real data. By training the generative function and/or the discriminative function on the one hand the generative function is configured to create synthetic data which is incorrectly classified by the discriminative function as real, on the other hand the discriminative function is configured to distinguish between real data and synthetic data generated by the generative function. In the notion of game theory, a generative adversarial model can be interpreted as a zero-sum game. The training of the generative function and/or of the discriminative function is based, in particular, on the minimization of a cost function.

By using a GA model, based on a set of training data synthetic data can be generated that has the same characteristics as the training data set. The training of the GA model can be based on data not being annotated (unsupervised learning), so that there is low effort in training a GA model.

Figure 8:
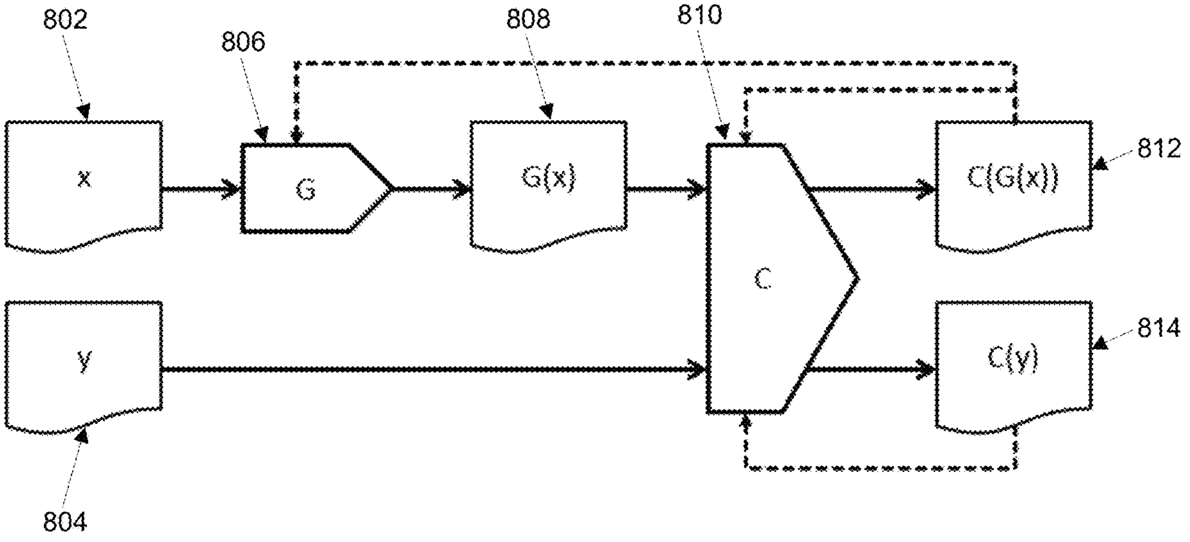
FIG. 8 shows a data flow diagram for using a generative adversarial network for creating synthetic output data to implement one or more embodiments.

FIG. 8 shows a data flow diagram according to an embodiment for using a generative adversarial network for creating synthetic output data G(x) 808 based on input data x 802 that is indistinguishable from real output data y 804, in accordance with one or more embodiments. The synthetic output data G(x) 808 has the same structure as the real output data y 804, but its content is not derived from real world data.

The generative adversarial network comprises a generator function G 806 and a classifier function C 810 which are trained jointly. The task of the generator function G 806 is to provide realistic synthetic output data G(x) 808 based on input data x 802, and the task of the classifier function C 810 is to distinguish between real output data y 804 and synthetic output data G(x) 808. In particular, the output of the classifier function C 810 is a real number between 0 and 1 corresponding to the probability of the input value being real data, so that an ideal classifier function would calculate an output value of C(y) 814≈1 for real data y 804 and C(G(x)) 812≈0 for synthetic data G(x) 808.

Within the training process, parameters of the generator function G 806 are adapted so that the synthetic output data G(x) 808 has the same characteristics as real output data y 804, so that the classifier function C 810 cannot distinguish between real and synthetic data anymore. At the same time, parameters of the classifier function C 810 are adapted so that it distinguishes between real and synthetic data in the best possible way. Here, the training relies on pairs comprising input data x 802 and the corresponding real output data y 804. Within a single training step, the generator function G 806 is applied to the input data x 802 for generating synthetic output data G(x) 808. Furthermore, the classifier function C 810 is applied to the real output data y 804 for generating a first classification result C(y) 814. Additionally, the classifier function C 810 is applied to the synthetic output data G(x) 808 for generating a second classification result C(G(x)) 812.

Adapting the parameters of the generative function G 806 and the classifier function C 810 is based on minimizing a cost function by using the backpropagation algorithm, respectively. In this embodiment, the cost function $K_C$ for the classifier function C 810 is $K_C \propto -\mathrm{BCE}(C(y), 1) - \mathrm{BCE}(C(G(x), 0)$, wherein BCE denotes the binary cross entropy defined as $\mathrm{BCE}(z, z') = z' \cdot \log(z) + (1-z') \cdot \log(1-z)$. By using this cost function, both wrongly classifying real output data as synthetic (indicated by C(y)≈0) and wrongly classifying synthetic output data as real (indicated as C(G(x)) 812≈1) increases the cost function $K_C$ to be minimized. Furthermore, the cost function $K_C$ for the generator function G 806 is $K_G \propto -\mathrm{BCE}(C(G(x), 1) = -\log(C(G(x))$. By using this cost function, correctly classified synthetic output data (indicated as C(G(x)) 812≈0) leads to an increase of the cost function $K_G$ to be minimized.

In particular, a recurrent machine learning model is a machine learning model whose output does not only depend on the input value and the parameters of the machine learning model adapted by the training process, but also on a hidden state vector, wherein the hidden state vector is based on previous inputs used on for the recurrent machine learning model. In particular, the recurrent machine learning model can comprise additional storage states or additional structures that incorporate time delays or comprise feedback loops.

In particular, the underlying structure of a recurrent machine learning model can be a neural network, which can be denoted as recurrent neural network. Such a recurrent neural network can be described as an artificial neural network where connections between nodes form a directed graph along a temporal sequence. In particular, a recurrent neural network can be interpreted as directed acyclic graph. In particular, the recurrent neural network can be a finite impulse recurrent neural network or an infinite impulse recurrent neural network (wherein a finite impulse network can be unrolled and replaced with a strictly feedforward neural network, and an infinite impulse network cannot be unrolled and replaced with a strictly feedforward neural network).

In particular, training a recurrent neural network can be based on the BPTT algorithm (acronym for "backpropagation through time"), on the RTRL algorithm (acronym for "real-time recurrent learning") and/or on genetic algorithms.

By using a recurrent machine learning model input data comprising sequences of variable length can be used. In particular, this implies that the method cannot be used only for a fixed number of input datasets (and needs to be trained differently for every other number of input datasets used as input), but can be used for an arbitrary number of input datasets. This implies that the whole set of training data, independent of the number of input datasets contained in different sequences, can be used within the training, and that training data is not reduced to training data corresponding to a certain number of successive input datasets.

Figure 9:
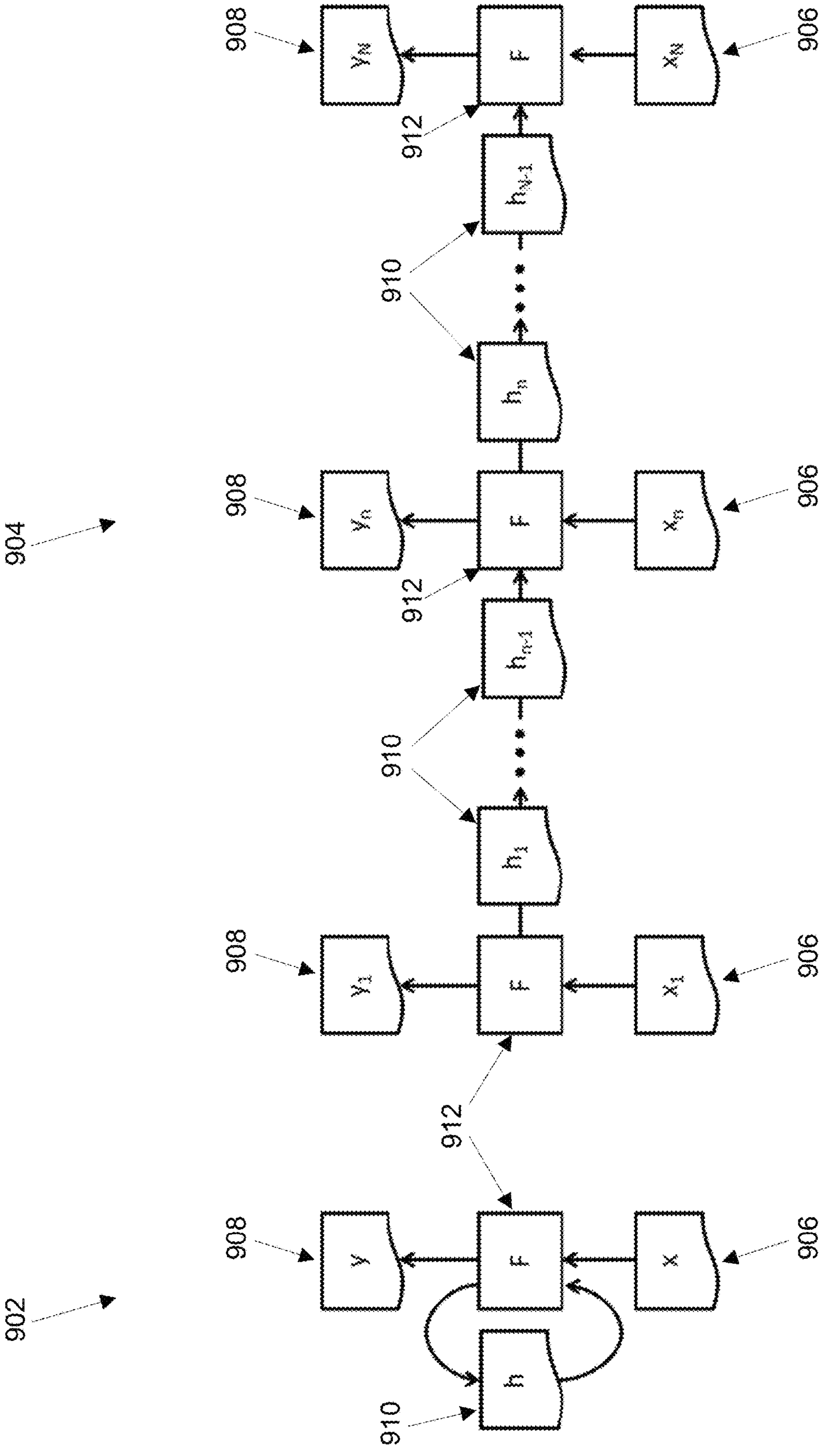
FIG. 9 shows a schematic structure of a recurrent machine learning model that may be used to implement one or more embodiments.

FIG. 9 shows the schematic structure of a recurrent machine learning model F, both in a recurrent representation 902 and in an unfolded representation 904, that may be used to implement one or more machine learning models described herein. The recurrent machine learning model takes as input several input datasets x, $x_1, \ldots, x_N$ 906 and creates a corresponding set of output datasets y, $y_1, \ldots, y_N$ 908. Furthermore, the output depends on a so-called hidden vector h, $h_1, \ldots, h_N$ 910, which implicitly comprises information about input datasets previously used as input for the recurrent machine learning model F 912. By using these hidden vectors h, $h_1, \ldots, h_N$ 910, a sequentiality of the input datasets can be leveraged.

In a single step of the processing, the recurrent machine learning model F 912 takes as input the hidden vector $h_{n-1}$ created within the previous step and an input dataset $x_n$. Within this step, the recurrent machine learning model F generates as output an updated hidden vector $h_n$ and an output dataset $y_n$. In other words, one step of processing calculates $(y_n, h_n) = F(x_n, h_{n-1})$, or by splitting the recurrent machine learning model F 912 into a part F (y) calculating the output data and F (h) calculating the hidden vector, one step of processing calculates $y_n = F^{(y)}(x_n, h_{n-1})$ and $h_n = F^{(h)}(x_n, h_{n-1})$. For the first processing step, $h_0$ can be chosen randomly or filled with all entries being zero. The parameters of the recurrent machine learning model F 912 that were trained based on training datasets before do not change between the different processing steps.

In particular, the output data and the hidden vector of a processing step depend on all the previous input datasets used in the previous steps. $y_n = F^{(y)}(x_n, F^{(h)}(x_{n-1}, h_{n-2}))$ and $h_n = F^{(h)}(x_n, F^{(h)}(x_{n-1}, h_{n-2}))$.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatuses, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatuses, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-5. Certain steps or functions of the methods and workflows described herein, including one or more of the steps or functions of FIGS. 1-5, may be performed by a server or by another processor in a network-based cloud-computing system. Certain steps or functions of the methods and workflows described herein, including one or more of the steps of FIGS. 1-5, may be performed by a client computer in a network-based cloud computing system. The steps or functions of the methods and workflows described herein, including one or more of the steps of FIGS. 1-5, may be performed by a server and/or by a client computer in a network-based cloud computing system, in any combination.

Systems, apparatuses, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 1002 that may be used to implement systems, apparatuses, and methods described herein is depicted in FIG. 10. Computer 1002 includes a processor 1004 operatively coupled to a data storage device 1012 and a memory 1010. Processor 1004 controls the overall operation of computer 1002 by executing computer program instructions that define such operations. The computer program instructions may be stored in data storage device 1012, or other computer readable medium, and loaded into memory 1010 when execution of the computer program instructions is desired. Thus, the method and workflow steps or functions of FIGS. 1-5 can be defined by the computer program instructions stored in memory 1010 and/or data storage device 1012 and controlled by processor 1004 executing the computer program instructions. For example, the computer program instructions can be implemented as computer executable code programmed by one skilled in the art to perform the method and workflow steps or functions of FIGS. 1-5. Accordingly, by executing the computer program instructions, the processor 1004 executes the method and workflow steps or functions of FIGS. 1-5. Computer 1002 may also include one or more network interfaces 1006 for communicating with other devices via a network. Computer 1002 may also include one or more input/output devices 1008 that enable user interaction with computer 1002 (e.g., display, keyboard, mouse, speakers, buttons, etc.).

Processor 1004 may include both general and special purpose microprocessors, and may be the sole processor or one of multiple processors of computer 1002. Processor 1004 may include one or more central processing units (CPUs), for example. Processor 1004, data storage device 1012, and/or memory 1010 may include, be supplemented by, or incorporated in, one or more application-specific integrated circuits (ASICs) and/or one or more field programmable gate arrays (FPGAs).

Data storage device 1012 and memory 1010 each include a tangible non-transitory computer readable storage medium. Data storage device 1012, and memory 1010, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1008 may include peripherals, such as a printer, scanner, display screen, etc. For example, input/output devices 1008 may include a display device such as a cathode ray tube (CRT) or liquid crystal display (LCD) monitor for displaying information to the user, a keyboard, and a pointing device such as a mouse or a trackball by which the user can provide input to computer 1002.

An image acquisition device 1014 can be connected to the computer 1002 to input image data (e.g., medical images) to the computer 1002. It is possible to implement the image acquisition device 1014 and the computer 1002 as one device. It is also possible that the image acquisition device 1014 and the computer 1002 communicate wirelessly through a network. In a possible embodiment, the computer 1002 can be located remotely with respect to the image acquisition device 1014.

Any or all of the systems, apparatuses, and methods discussed herein may be implemented using one or more computers such as computer 1002.

One skilled in the art will recognize that an implementation of an actual computer or computer system may have other structures and may contain other components as well, and that FIG. 10 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving 1) an initial image depicting a current position of a medical image acquisition device and 2) at least one of a target image depicting a target position of the medical image acquisition device or text-based instructions for navigating to the target position of the medical image acquisition device; extracting features from the at least one of the target image or the text-based instructions respectively using at least one of a machine learning based image encoder or a machine learning based text encoder, wherein the machine learning based image encoder and the machine learning based text encoder are trained to generate corresponding features for training target images and training text-based instructions for same target positions; determining one or more actions for navigating the medical image acquisition device from the current position towards the target position according to a learned policy based on the initial image and the extracted features; and outputting the one or more actions.

Illustrative embodiment 2. The computer-implemented method of illustrative embodiment 1, wherein the machine learning based image encoder and the machine learning based text encoder are trained to maximize a similarity between the features extracted from the training target images and the features extracted from the training text-based instructions.

Illustrative embodiment 3. The computer-implemented method of any one of illustrative embodiments 1-2, wherein the machine learning based image encoder and the machine learning based text encoder are trained to minimize a similarity between the features extracted from the training target images and features extracted from randomly sampled training text-based instructions.

Illustrative embodiment 4. The computer-implemented method of any one of illustrative embodiments 1-3, wherein determining one or more actions for navigating the medical image acquisition device from the current position towards the target position according to a learned policy based on the initial image and the extracted features comprises: determining the one or more actions using a machine learning based policy network, the machine learning based policy network receiving as input the initial image and the extracted features and generating as output the one or more actions.

Illustrative embodiment 5. The computer-implemented method of any one of illustrative embodiments 1-4, wherein determining one or more actions for navigating the medical image acquisition device from the current position towards the target position according to a learned policy based on the initial image and the extracted features comprises: extracting features from the initial image using another machine learning based image encoder; and determining the one or more actions using a machine learning based policy network, the machine learning based policy network receiving as input the features extracted from the initial image and the features extracted from the at least one of the target image or the text-based instructions and generating as output the one or more actions.

Illustrative embodiment 6. The computer-implemented method of any one of illustrative embodiments 1-5, wherein determining one or more actions for navigating the medical image acquisition device from the current position towards the target position according to a learned policy based on the initial image and the extracted features comprises: determining the one or more actions using a machine learning based policy network, wherein the machine learning based policy network is trained based on training initial image and features extracted from the training target images using the machine learning based image encoder to learn the learned policy.

Illustrative embodiment 7. The computer-implemented method of any one of illustrative embodiments 1-6, wherein the training text-based instructions are generated based on trajectory descriptions representing paths between initial images and target images, the trajectory descriptions generated by: segmenting one or more anatomical objects from the initial images and the target images; generating summaries of the initial images and the target images based on the segmentations; and generating the trajectory descriptions based on the generated summaries of the initial images and the target images using a language model.

Illustrative embodiment 8. The computer-implemented method of any one of illustrative embodiments 1-7, wherein the medical image acquisition device comprises a transducer of an ultrasound imaging system.

Illustrative embodiment 9. The computer-implemented method of any one of illustrative embodiments 1-8, wherein the text-based instructions comprise natural language text.

Illustrative embodiment 10. An apparatus comprising: means for receiving 1) an initial image depicting a current position of a medical image acquisition device and 2) at least one of a target image depicting a target position of the medical image acquisition device or text-based instructions for navigating to the target position of the medical image acquisition device; means for extracting features from the at least one of the target image or the text-based instructions respectively using at least one of a machine learning based image encoder or a machine learning based text encoder, wherein the machine learning based image encoder and the machine learning based text encoder are trained to generate corresponding features for training target images and training text-based instructions for same target positions; means for determining one or more actions for navigating the medical image acquisition device from the current position towards the target position according to a learned policy based on the initial image and the extracted features; and means for outputting the one or more actions.

Illustrative embodiment 11. The apparatus of any illustrative embodiment 10, wherein the machine learning based image encoder and the machine learning based text encoder are trained to maximize a similarity between the features extracted from the training target images and the features extracted from the training text-based instructions.

Illustrative embodiment 12. The apparatus of any one of illustrative embodiments 10-11, wherein the machine learning based image encoder and the machine learning based text encoder are trained to minimize a similarity between the features extracted from the training target images and features extracted from randomly sampled training text-based instructions.

Illustrative embodiment 13. The apparatus of any one of illustrative embodiments 10-12, wherein the means for determining one or more actions for navigating the medical image acquisition device from the current position towards the target position according to a learned policy based on the initial image and the extracted features comprises: means for determining the one or more actions using a machine learning based policy network, the machine learning based policy network receiving as input the initial image and the extracted features and generating as output the one or more actions.

Illustrative embodiment 14. The apparatus of any one of illustrative embodiments 10-13, wherein the means for determining one or more actions for navigating the medical image acquisition device from the current position towards the target position according to a learned policy based on the initial image and the extracted features comprises: means for extracting features from the initial image using another machine learning based image encoder; and means for determining the one or more actions using a machine learning based policy network, the machine learning based policy network receiving as input the features extracted from the initial image and the features extracted from the at least one of the target image or the text-based instructions and generating as output the one or more actions.

Illustrative embodiment 15. A non-transitory computer-readable storage medium comprising instructions which, when executed by a computer, cause the computer to carry out operations comprising: receiving 1) an initial image depicting a current position of a medical image acquisition device and 2) at least one of a target image depicting a target position of the medical image acquisition device or text-based instructions for navigating to the target position of the medical image acquisition device; extracting features from the at least one of the target image or the text-based instructions respectively using at least one of a machine learning based image encoder or a machine learning based text encoder, wherein the machine learning based image encoder and the machine learning based text encoder are trained to generate corresponding features for training target images and training text-based instructions for same target positions; determining one or more actions for navigating the medical image acquisition device from the current position towards the target position according to a learned policy based on the initial image and the extracted features; and outputting the one or more actions.

Illustrative embodiment 16. The non-transitory computer-readable storage medium of illustrative embodiment 15, wherein the machine learning based image encoder and the machine learning based text encoder are trained to maximize a similarity between the features extracted from the training target images and the features extracted from the training text-based instructions and minimize a similarity between the features extracted from the training target images and features extracted from randomly sampled training text-based instructions.

Illustrative embodiment 17. The non-transitory computer-readable storage medium of any one of illustrative embodiments 15-16, wherein determining one or more actions for navigating the medical image acquisition device from the current position towards the target position according to a learned policy based on the initial image and the extracted features comprises: determining the one or more actions using a machine learning based policy network, wherein the machine learning based policy network is trained based on training initial images and features extracted from the training target images using the machine learning based image encoder to learn the learned policy.

Illustrative embodiment 18. The non-transitory computer-readable storage medium of any one of illustrative embodiments 15-17, wherein the training text-based instructions are generated based on trajectory descriptions representing paths between initial images and target images, the trajectory descriptions generated by: segmenting one or more anatomical objects from the initial images and the target images; generating summaries of the initial images and the target images based on the segmentations; and generating the trajectory descriptions based on the generated summaries of the initial images and the target images using a language model.

Illustrative embodiment 19. The non-transitory computer-readable storage medium of any one of illustrative embodiments 15-18, wherein the medical image acquisition device comprises a transducer of an ultrasound imaging system.

Illustrative embodiment 20. The non-transitory computer-readable storage medium of any one of illustrative embodiments 15-19, wherein the text-based instructions comprise natural language text.

The invention claimed is:

1. A computer-implemented method comprising:

jointly training a machine learning based image encoder and a machine learning based text encoder using one or more training target images depicting a particular target position and one or more training text-based instructions for navigating to the particular target position, wherein image features extracted from the one or more training target images by the machine learning based image encoder correspond to text features extracted from the one or more training text-based instructions by the machine learning based text encoder;

receiving 1) an initial image depicting a current position of a medical image acquisition device and 2) at least one of a target image depicting a specific target position of the medical image acquisition device or text-based instructions for navigating to the specific target position of the medical image acquisition device;

extracting features from the at least one of the target image or the text-based instructions respectively using at least one of the trained machine learning based image encoder or the trained machine learning based text encoder;

determining one or more actions for navigating the medical image acquisition device from the current position towards the specific target position using a machine learning based policy network, wherein the machine learning based policy network receives as input the initial image and the extracted features, and wherein the one or more actions comprise a change in one or more of a position, location, or orientation of the medical image acquisition device; and outputting, by the machine learning based policy network, the one or more actions.

2. The computer-implemented method of claim 1, wherein jointly training a machine learning based image encoder and a machine learning based text encoder using one or more training target images depicting a particular target position and one or more training text-based instructions for navigating to the particular target position comprises:

jointly training the machine learning based image encoder and the machine learning based text encoder to maximize a similarity between the image features extracted from the one or more training target images and the text features extracted from the one or more training text-based instructions.

3. The computer-implemented method of claim 1, wherein jointly training a machine learning based image encoder and a machine learning based text encoder using one or more training target images depicting a particular target position and one or more training text-based instructions for navigating to the particular target position comprises:

jointly training the machine learning based image encoder and the machine learning based text encoder to minimize a similarity between the image features extracted from the one or more training target images and the text features extracted from randomly sampled ones of the one or more training text-based instructions.

4. The computer-implemented method of claim 1, wherein determining one or more actions for navigating the medical image acquisition device from the current position towards the specific target position using a machine learning based policy network comprises:

extracting features from the initial image using another machine learning based image encoder, the machine learning based policy network receiving as input the features extracted from the initial image and the features extracted from the at least one of the target image or the text-based instructions and generating as output the one or more actions.

5. The computer-implemented method of claim 1, wherein determining one or more actions for navigating the medical image acquisition device from the current position towards the specific target position using a machine learning based policy network comprises:

determining the one or more actions according to a learned policy using the machine learning based policy network, wherein the machine learning based policy network is trained based on training initial images and the image features extracted from the one or more training target images using the machine learning based image encoder to learn the learned policy.

6. The computer-implemented method of claim 1, wherein the one or more training text-based instructions are generated based on trajectory descriptions representing paths between initial images and target images, the trajectory descriptions generated by:

segmenting one or more anatomical objects from the initial images and the target images;

generating summaries of the initial images and the target images based on the segmentations; and generating the trajectory descriptions based on the generated summaries of the initial images and the target images using a language model.

7. The computer-implemented method of claim 1, wherein the medical image acquisition device comprises a transducer of an ultrasound imaging system.

8. The computer-implemented method of claim 1, wherein the text-based instructions comprise natural language text.

9. An apparatus comprising:

means for jointly training a machine learning based image encoder and a machine learning based text encoder using one or more training target images depicting a particular target position and one or more training text-based instructions for navigating to the particular target position, wherein image features extracted from the one or more training target images by the machine learning based image encoder correspond to text features extracted from the one or more training text-based instructions by the machine learning based text encoder;

means for receiving 1) an initial image depicting a current position of a medical image acquisition device and 2) at least one of a target image depicting a specific target position of the medical image acquisition device or text-based instructions for navigating to the specific target position of the medical image acquisition device;

means for extracting features from the at least one of the target image or the text-based instructions respectively using at least one of the trained machine learning based image encoder or the trained machine learning based text encoder;

means for determining one or more actions for navigating the medical image acquisition device from the current position towards the specific target position using a machine learning based policy network, wherein the machine learning based policy network receives as input the initial image and the extracted features, and wherein the one or more actions comprise a change in one or more of a position, location, or orientation of the medical image acquisition device; and means for outputting, by the machine learning based policy network, the one or more actions.

10. The apparatus of claim 9, wherein the means for jointly training a machine learning based image encoder and a machine learning based text encoder using one or more training target images depicting a particular target position and one or more training text-based instructions for navigating to the particular target position comprises:

means for jointly training the machine learning based image encoder and the machine learning based text encoder to maximize a similarity between the image features extracted from the one or more training target images and the text features extracted from the one or more training text-based instructions.

11. The apparatus of claim 9, wherein the means for jointly training a machine learning based image encoder and a machine learning based text encoder using one or more training target images depicting a particular target position and one or more training text-based instructions for navigating to the particular target position comprises:

means for jointly training the machine learning based image encoder and the machine learning based text encoder to minimize a similarity between the image features extracted from the one or more training target images and the text features extracted from randomly sampled ones of the one or more training text-based instructions.

12. The apparatus of claim 9, wherein the means for determining one or more actions for navigating the medical image acquisition device from the current position towards the specific target position using a machine learning based policy network comprises:

means for extracting features from the initial image using another machine learning based image encoder, the machine learning based policy network receiving as input the features extracted from the initial image and the features extracted from the at least one of the target image or the text-based instructions and generating as output the one or more actions.

13. A non-transitory computer-readable storage medium comprising instructions which, when executed by a computer, cause the computer to carry out operations comprising:

jointly training a machine learning based image encoder and a machine learning based text encoder using one or more training target images depicting a particular target position and one or more training text-based instructions for navigating to the particular target position, wherein image features extracted from the one or more training target images by the machine learning based image encoder correspond to text features extracted from the one or more training text-based instructions by the machine learning based text encoder;

receiving 1) an initial image depicting a current position of a medical image acquisition device and 2) at least one of a target image depicting a specific target position of the medical image acquisition device or text-based instructions for navigating to the specific target position of the medical image acquisition device;

extracting features from the at least one of the target image or the text-based instructions respectively using at least one of the trained machine learning based image encoder or the trained machine learning based text encoder;

determining one or more actions for navigating the medical image acquisition device from the current position towards the specific target position using a machine learning based policy network, wherein the machine learning based policy network receives as input the initial image and the extracted features, and wherein the one or more actions comprise a change in one or more of a position, location, or orientation of the medical image acquisition device; and outputting, by the machine learning based policy network, the one or more actions.

14. The non-transitory computer-readable storage medium of claim 13, wherein jointly training a machine learning based image encoder and a machine learning based text encoder using one or more training target images depicting a particular target position and one or more training text-based instructions for navigating to the particular target position comprises:

jointly training the machine learning based image encoder and the machine learning based text encoder to maximize a similarity between the image features extracted from the one or more training target images and the text features extracted from the one or more training text-based instructions and to minimize a similarity between the image features extracted from the one or more training target images and the text features extracted from randomly sampled ones of the one or more training text-based instructions.

15. The non-transitory computer-readable storage medium of claim 13, determining one or more actions for navigating the medical image acquisition device from the current position towards the specific target position using the machine learning based policy network comprises:

determining the one or more actions according to a learned policy using the machine learning based policy network, wherein the machine learning based policy network is trained based on training initial images and the image features extracted from the one or more training target images using the machine learning based image encoder to learn the learned policy.

16. The non-transitory computer-readable storage medium of claim 13, wherein the training text-based instructions are generated based on trajectory descriptions representing paths between initial images and target images, the trajectory descriptions generated by:

segmenting one or more anatomical objects from the initial images and the target images;

generating summaries of the initial images and the target images based on the segmentations; and generating the trajectory descriptions based on the generated summaries of the initial images and the target images using a language model.

17. The non-transitory computer-readable storage medium of claim 13, wherein the medical image acquisition device comprises a transducer of an ultrasound imaging system.

18. The non-transitory computer-readable storage medium of claim 13, wherein the text-based instructions comprise natural language text.

* * * * *